(12) United States Patent
Yuen

(10) Patent No.: US 6,677,131 B2
(45) Date of Patent: Jan. 13, 2004

(54) WELL FRAME INCLUDING CONNECTORS FOR BIOLOGICAL FLUIDS

(75) Inventor: Po Ki Yuen, Corning, NY (US)

(73) Assignee: Corning Incorporated, Corning, NY (US)

( * ) Notice: Subject to any disclaimer, the term of this patent is extended or adjusted under 35 U.S.C. 154(b) by 16 days.

(21) Appl. No.: 09/854,834

(22) Filed: May 14, 2001

(65) Prior Publication Data

US 2002/0168624 A1 Nov. 14, 2002

(51) Int. Cl.$^7$ .............................. C12Q 1/02; C12M 1/36
(52) U.S. Cl. ...................... 435/29; 435/91.2; 435/286.5; 435/287.2; 435/288.3
(58) Field of Search ...................... 435/4, 287.2, 288.3, 435/305.3, 305.4, 283.1, 29, 91.2, 289.5

(56) References Cited

U.S. PATENT DOCUMENTS

| | | | |
|---|---|---|---|
| 5,100,775 A | 3/1992 | Smyczek et al. ............... 435/6 |
| 5,188,963 A | 2/1993 | Stapleton ..................... 435/299 |
| 5,346,672 A | 9/1994 | Stapleton et al. ........... 422/102 |
| 5,451,500 A | 9/1995 | Stapleton ....................... 435/6 |
| 5,681,741 A | * 10/1997 | Atwood et al. ........... 435/287.2 |
| 5,922,604 A | 7/1999 | Stapleton et al. ............. 436/46 |
| 6,114,122 A | * 9/2000 | Besemer et al. ............... 435/6 |
| 6,159,727 A | 12/2000 | Bochkariov ............... 435/287.2 |
| 6,258,593 B1 | * 7/2001 | Schembri et al. ........ 435/287.2 |
| 6,287,768 B1 | 9/2001 | Chenchik et al. |
| 6,422,249 B1 | * 7/2002 | Certa et al. ............. 134/168 R |
| 2002/0061529 A1 | * 5/2002 | Bridgham et al. ............. 435/6 |
| 2002/0150933 A1 | * 10/2002 | Ehricht et al. ................. 435/6 |

OTHER PUBLICATIONS

Deniz Armani et al., "Re–Configurable Fluid Circuits by PDMS Elastomer Micromachining", 12th International Conference on MEMS, MEMS 99, pp. 222–227, Orland, FL, 1998.

* cited by examiner

Primary Examiner—David A. Redding
(74) Attorney, Agent, or Firm—Scott S. Servilla; Vincent T. Kung

(57) ABSTRACT

A device, a kit and a method for the hybridization reactions between biomolecules are disclosed. The invention relates to a hybridization chamber including a generally planar substrate which includes a specimen area containing at least one biomolecule. The hybridization chamber also includes a frame surrounding at least a portion of the specimen area. The frame defines walls of a well for holding a fluid when the frame is in contact with the substrate. The frame includes a connector adapted to connect to tubing for supplying fluids to the well. Tubing connected to the connectors may be used to supply wash fluid and hybridization fluid, and waste tubing may be connected to a second connector for removing waste material from the well.

13 Claims, 5 Drawing Sheets

WELL FRAME INCLUDING CONNECTORS FOR BIOLOGICAL FLUIDS

FIELD OF THE INVENTION

This invention relates to devices, kits and methods for fluid processing of biological material, particularly processing biological material with controlled and minimal fluid quantities. The devices, kits and methods of the invention are particularly useful for hybridization of biomolecules, which may be bound to a substrate.

BACKGROUND OF THE INVENTION

High-throughput processing of biological material using fluids containing biomolecules is widely used in several fields. The processing of biological material surface mounted on planar substrates such as slides is known and used in various procedures. For example, biotechnology, biochemistry, molecular biology, molecular genetics, cytogenetics, cell biology, pharmacology, and immunology, are examples of fields in which such procedures have been used for analytical and diagnostic purposes. In a typical procedure, a slide containing immobilized biological material is contacted with a variety of fluids, and usually involves a number of processing steps. It is essential that the processing steps are carried out properly to obtain repeatable and comparable results.

Two examples of such procedures include hybridization of slide-bound nucleic acid probes with labeled targets that incorporate complementary nucleotide sequences and staining of biological material. In a procedure involving the staining of slide mounted specimens of biological materials, the prepared slides may be dipped successively into a series of small vessels or jars, each about 0.2 to about 2 liters in volumetric capacity, and each containing a particular liquid treating composition, such as washing agents, buffers, dehydrating agents, dyes and other solutions. Dye materials may be used to highlight different cells, structures of cells, intracellular structures, and cellular products. Resulting dyed slides may be washed and dried, possibly stored, and then microscopically examined. Selective staining procedures using specific antibody or gene probes have been developed and are advantageously highly specific and sensitive. However, such procedures require many successive steps to be carried out.

Another example of a procedure that utilizes slide-mounted biological materials is hybridization of biomolecules. Screening of biomolecules such as nucleic acids, protein sequences of amino acids, carbohydrates, lipids and living cells containing biomolecules provides information about changes in physiological, biochemical and molecular interactions of biological samples at the cellular and/or subcellular level. Techniques such as hybridization utilize an analyte and a complementary binding entity that form a bound pair of the analyte and the binding entity. Such hybridization can be performed in solution, or alternatively, the analyte can be immobilized on a support such as a glass slide and contacted with a solution containing a binding entity. Typically a pattern or an array of different analytes (usually called probes) are immobilized on a glass slide, and a solution containing a binding entity (usually called the target) contacts the array. Unbound binding entities can be washed from the slide, and various types of analytical technique involving, for example, phosphorescence, fluorescence, and radioactivity, can be performed to determine which specific sites or probes were bound to the target or targets.

In a more specific example, the high throughput screening of nucleic acids is typically performed by attaching base pairs of nucleic acid sequences in an array of locations on a glass plate or slide. Each spot location provides an address for later reference to each spot of nucleic acid. Hybridization techniques utilize markers such as radioactive or fluorescent compounds to label particular nucleic acid sequences that are complementary to the nucleic acid sequences on the glass slide. Signal measurement equipment is then utilized to measure each address on the array to determine if the labeled sequences have attached to the complementary sequence on the glass slide. The resulting slide is examined using an evaluation procedure such as, for example, microscopy, autoradiography, fluorescence measurement, photon emission, or the like. A single hybridization procedure may involve as many as thirty or more controlled step sequences.

Since multi-step processing of slide mounted biological materials typically involves numerous slides and a variety of process liquids and steps, it may be difficult to control the identical treatment of all slides. An additional concern in such processes is that some processing liquids, such as liquids containing nucleotides and other biomolecules, are very costly and must be used in small volumes.

Hybridization reactions are usually carried out in fluid-containing structures such as wells, bottles and other structures designed to contain the target-containing hybridization solution and a substrate containing an array of biomolecular probes. Conventional hybridization chamber devices, particularly hybridization chambers used with microarrays printed on a glass or plastic slide have several shortcomings.

For example, referring to FIGS. 1–7, which shows a typical and commercially available hybridization chamber assembly that includes three layers and a glass slide 10, which is shown in FIG. 1. The glass slide is provided with an array of biomolecules 12 arranged thereon, or an array of biomolecules may be printed on the surface of the glass slide 10. An example of a suitable slide for printing microarrays of biomolecules such as DNA is a CMT-GAPS™ coated slide available from the assignee of the present invention. Referring now to FIG. 3, a frame 14 for a commercially available hybridization chamber frame typically includes three layers. The first layer is a cover sheet 16, which may be made from glass or plastic and may include an inlet opening 18 and an outlet opening 20. The frame includes a second frame layer 22, which typically includes an adhesive backing and is attached to a disposable backing sheet 24.

According to known hybridization procedures, the slide 10 containing an array of biomolecules 12 immobilized on the surface of the slide is typically washed separately before attachment of the hybridization chamber frame. Referring to FIG. 4, after the slide 10 has been washed and dried, the adhesive backing sheet 24 is peeled from the frame layer 22 and the frame layer 22 and cover sheet 16 are positioned over the microarray of biomolecules 12 on the slide 10. Referring to FIG. 5, the frame layer 22 and cover sheet 10 are placed over the microarray of biomolecules 12 to surround the biomolecules and form a well structure 26 with the slide 10.

As shown in FIG. 6, a mixture of hybridization solution containing target molecules is injected in the inlet opening 18 with a pipette 28 or other suitable fluid injection device. Excess fluid may flow out of the outlet opening 20. After injection of the fluid, the hybridization chamber including the frame layer 22, the cover sheet 16 and the slide 10 are left for a time and under conditions to allow hybridization of the target molecules in the hybridization solution and probe biomolecules 12 on the slide 10. Referring now to FIG. 7, the frame layer 22 and the cover sheet 16 are removed from the slide 10, and additional processing steps such as post hybridization washing of the slide 10 containing the biomolecules are performed. Thereafter, the slide 10 is scanned and analyzed.

As evidenced by the above discussion, the delivery and removal of fluids to a hybridization chamber as shown in FIGS. 1–7 is not designed for rapid processing of slide-mounted material. It would be advantageous to provide a chamber frame having connectors that could be readily attached to standard laboratory tubing to facilitate the supply and removal of fluids from the well. Such a chamber would facilitate processing such slide-mounted material in a replicable manner. It would also be useful if the delivery and removal of fluids from such chambers and washing of the slide containing biological material could be automated and did not require laboratory personnel to handle the chambers to perform each step. Still further, there is a need in the art for devices and methods that utilize minimal amounts of processing fluids and agents particularly with regard to hybridization solutions containing target biomolecules.

SUMMARY OF THE INVENTION

Accordingly, the present invention generally provides methods, devices and kits for performing biological experiments using fluids. The devices of the invention include a generally planar substrate including a specimen area containing at least one biomolecule. An example of such a planar substrate is a slide containing a microarray of biomolecules. The devices of the present invention further include a frame surrounding at least a portion of the specimen area. The frame defines walls of a well for holding a fluid solution when the frame is in contact with the substrate and the frame including a connector adapted to connect to tubing for supplying fluids to the well.

The devices of the present invention are particularly suitable for use as biomolecular hybridization chambers, such as the type used in hybridization of nucleic acids. According to one aspect of the invention, the connectors are integrally formed with the frame. According to another aspect of the invention, the connectors can be any suitable type for connection with fluid supply tubing. Examples of such connectors include, but are not limited to male luer fittings, female luer fittings, flanged fittings, flangeless fittings, threaded fittings and barbed fittings.

According to another aspect of the invention, the frame includes at least two connectors adapted to connect to tubing for supplying fluids to the well. In this aspect, one of the least two fittings is connected to supply tubing for supplying reagents to the well and one of the at least two fittings is connected to waste tubing for removing fluids from the well.

In another aspect of the invention, the frame is manufactured from an elastomeric material that forms a fluid tight seal with the generally planar substrate. Preferably, the elastomeric material is silicone rubber, poly(dimethylsiloxane) (PDMS), and combinations thereof. PDMS is a particularly preferred material. It is preferred that a material is used so that the frame can be fabricated in relatively small dimensions to provide a frame dimensioned so that the depth of the well is less than 100 microns.

Another aspect of the invention involves a kit for performing experiments with biological materials using fluids including the generally planar substrate and the frame including connectors. Such kits can be utilized to carry out hybridization chamber assays. In this aspect, the kit may further include a slide for printing a high density microarray of biomolecules, or alternatively, a pre-printed DNA micro array.

In another aspect of the invention, a method of performing a hybridization assay is provided. The method includes the steps of providing a generally planar substrate including a specimen area containing at least one biomolecule and a frame including a connector adapted to connect to tubing for supplying fluids to the well. The method further includes the step of placing the frame in contact with the substrate so that the frame surrounds at least a portion of the specimen area and the frame and the substrate define a well for holding a solution.

Another aspect of the invention involves providing a frame including at least two connectors adapted to be connected to tubing. In this aspect, supply tubing may be connected to one of the connectors to supply fluids to the well and waste tubing may be connected to one of the connectors to remove fluids from the well. A further aspect of the invention involves supplying wash fluid to the well through the supply tubing and removing the wash fluid from the well through the waste tubing and supplying hybridization fluid to the well through the supply line. According to this aspect, hybridization material from the well can be removed through the waste tubing.

The invention provides a device, a kit and a method for performing biological experiments. The device allows such experiments to be performed with control over the amount of fluid utilized during such experiments and minimizes the waste of such fluids. The device facilitates the delivery of fluids to a specimen using standard tubing that connects to the connectors included in the hybridization frame. In addition, the connectors associated with frame, which can be connected to standard laboratory tubing, enables faster throughput of samples, which in turn facilitates high throughput screening of biomolecules.

Another advantage of the present invention is that the delivery of hybridization fluid and washing of microarray slides can be efficiently performed without having to remove the hybridization chamber frame. The hybridization solutions and wash fluids can be conveniently delivered via tubing through the connectors included with the hybridization frame. The method requires less laboratory worker skill and handling of reagents, which will lower the cost of laboratory processing and minimize the chance of human error in mishandling samples or possibly using the wrong hybridization solution during testing. Additional advantages of the invention will be set forth in the following detailed description. It is to be understood that both the foregoing general description and the following detailed description are exemplary and are intended to provide further explanation of the invention as claimed.

DETAILED DESCRIPTION

The invention relates devices, kits and methods for performing biological experiments with liquids. The invention is useful for performing hybridization assays on slide-mounted biomolecules. The invention is particularly useful for, but not limited to, performing hybridization assays on microarrays of biomolecules, such as nucleic acids.

Figure 1:
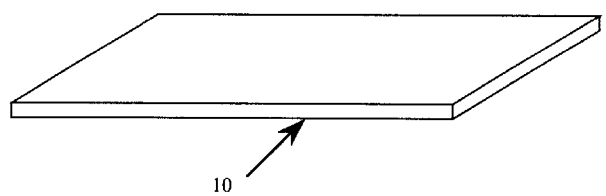
FIG. 1 is a perspective view of showing a slide for printing an array of biomolecules in accordance with a prior art method.
Figure 2:
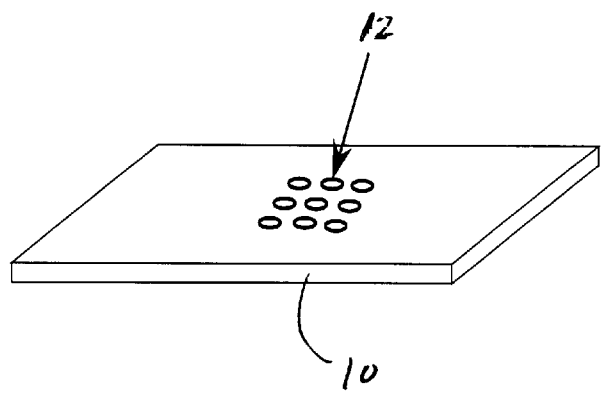
FIG. 2 is a perspective view showing a slide with biomolecules printing on the surface of the slide in accordance with a prior art method.
Figure 3:
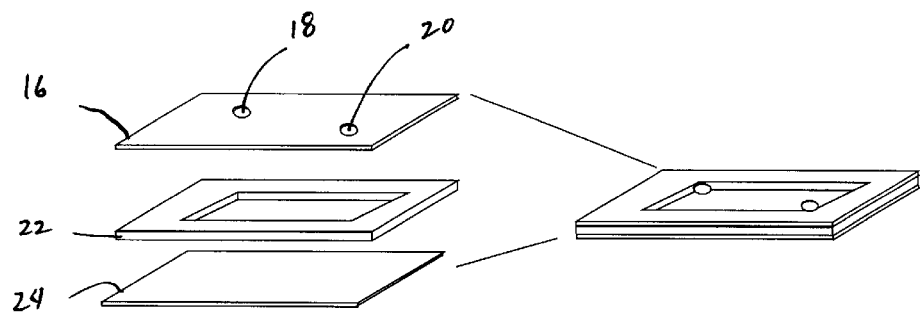
FIG. 3 is a perspective view of a prior art hybridization chamber frame structure.
Figure 4:
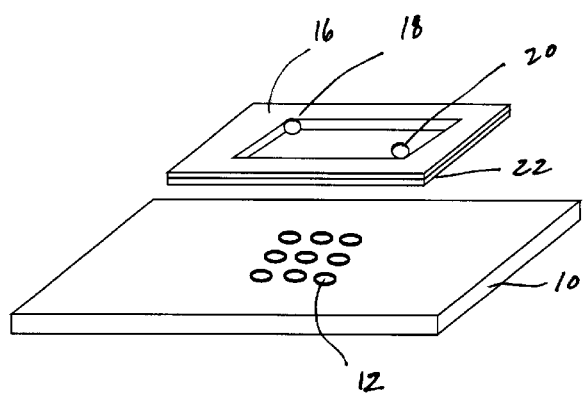
FIG. 4 is a perspective view showing a prior art hybridization frame structure positioned over a slide.
Figure 5:
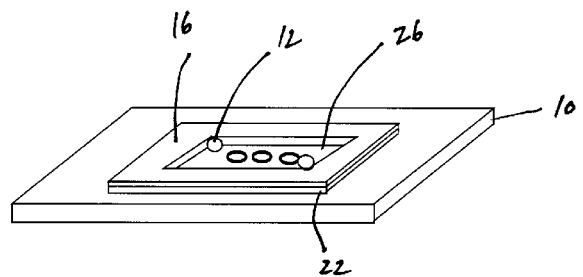
FIG. 5 is a perspective view showing a prior art hybridization frame structure attached to a slide to provide a hybridization chamber.
Figure 6:
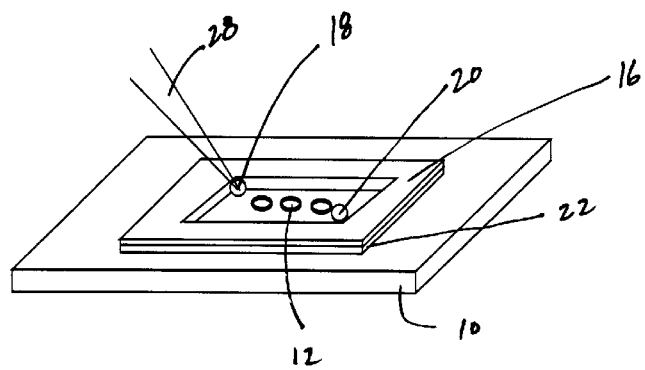
FIG. 6 is a perspective view showing injection of a fluid into a prior art hybridization chamber.
Figure 7:
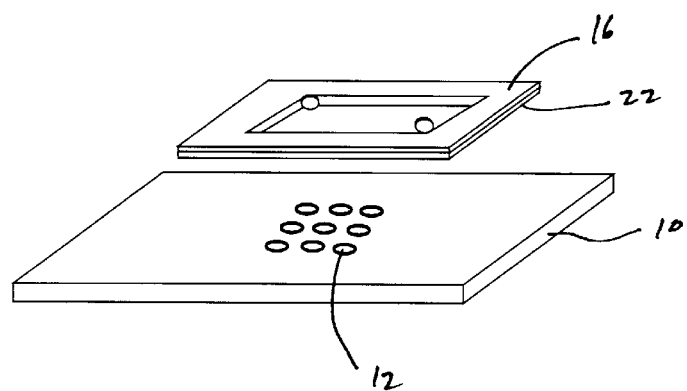
FIG. 7 is a perspective view showing removal of a prior art hybridization chamber frame structure from a slide.
Figure 8:
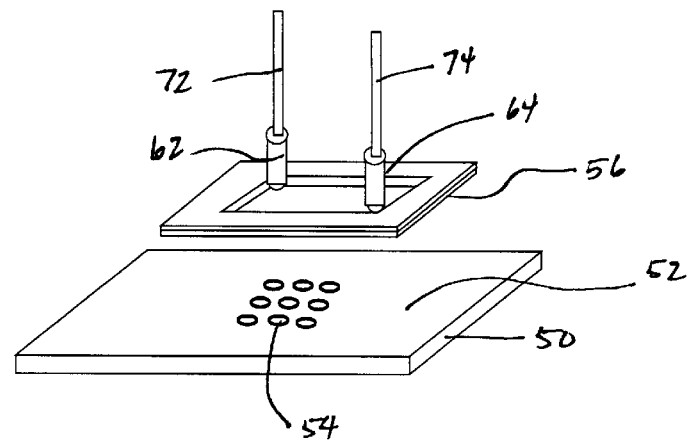
FIG. 8 is a perspective view of showing a frame including connectors positioned over a substrate according to one aspect of the invention.

Referring to FIG. 8, one aspect of the invention relates to a biomolecular hybridization chamber including a generally planar substrate 50, which includes a specimen area 52 containing at least one biomolecule 54. The substrate is preferably made from materials such as polymers, polystyrene, polypropylene, UV transparent film, glass, metal and combinations thereof.

Figure 9:
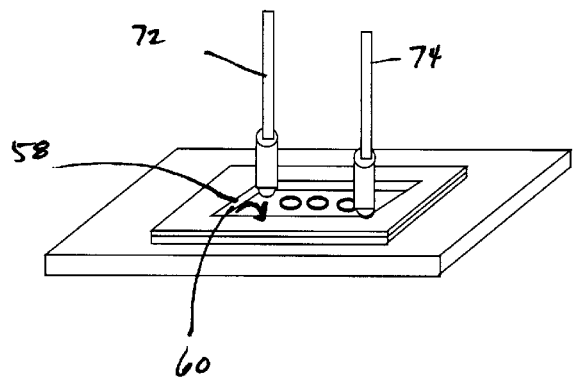
FIG. 9 is a perspective view showing the frame in FIG. 8 attached to the substrate according to another aspect of the invention.

The hybridization chamber further includes a frame 56 that, when attached to the substrate 50, surrounds at least a portion of the specimen area 52. When the frame 56 is attached to the substrate 50, the frame 56 defines walls 58 of a well 60 for holding a fluid. The frame 56 includes at least one connector 62 adapted to connect tubing 72 for supplying fluids to the well. Preferably, the frame includes at least two connectors, and as shown in FIGS. 8 and 9, and a second connector 64 is adapted to connect to a second piece of tubing 74. According to this aspect of the invention, the first connector 62 and tubing 72 may be connected to a supply of fluid and the second connector 64 and tubing 74 may be connected to a waste line.

It will be understood that any suitable laboratory equipment can be utilized to supply and remove fluids from the well 60. For example, a variety of equipment such as pumps, vacuum lines, reservoirs, etc. can be connected to the hybridization chamber via tubing that can be connected to the connectors on the hybridization chamber frame 56. Such connection is further facilitated by selecting connectors have standard fittings, such as, but not limited to male luer fittings, female luer fittings, flanged fittings, flangeless fittings, barbed fittings, threading fittings, etc. Such fittings are available from a number of suppliers, such as Upchurch Scientific, Oak Harbor, Wash.

According to another aspect of the invention the frame is manufactured from an elastomeric material such as poly (dimethylsiloxane) (PDMS) or silicone rubber. Preferably, the elastomeric material is capable of forming a fluid tight seal with a conventional slide material such as glass or plastic. Preferably, the material used is transparent, to allow for observation of the fluid flow in and out of the hybridization chamber and to allow for observation of the hybridization experiment. The frame may further include an adhesive layer or adhesive material on the surface of the frame that contacts the slide, to enable the frame to adhere to the slide. Preferably, however, the material selected for the frame is capable of self-adhering the slide.

PDMS is a particularly preferred material for manufacturing the frame because it is a flexible, elastomeric material that can be reversible deformed without permanent distortion. In addition, PDMS can be molded in extremely small shapes, with feature sizes as small as 20 microns. PDMS is also a very durable material and chemically inert. Furthermore, it is non-toxic, abundantly available commercially and inexpensive.

The chamber frames of the present invention including the connectors can be manufactured according to a wide variety of methods. The chamber frame can be designed using a computer drawing package. A mask of the design can be created using conventional photolithographic techniques. For example, contact photolithography can be utilized to provide a positive relief of photoresist on a glass or silicon substrate. Conventional micromachining techniques can be used to fabricate a master substrate carrying a positive surface relief of the chamber frame. Standard connectors can be placed in the master substrate to define inlet and outlet connections for the chamber frame. A prepolymer of the frame material, which is preferably PDMS, is then cast into the master substrate and cured. The polymer replica of the frame including the connectors can then be utilized to form a hybridization chamber on a generally planar substrate such a glass slide containing a microarray of biomolecules. Tubing can be attached to the inlets and outlets for supplying and removing fluids from the well defined by the chamber frame walls and the substrate. Other techniques may be used to provide the frame structures of the invention. For example, high resolution printing techniques described by Duffy et al, in the article Rapid Prototyping of Microfluidic Systems in Poly(dimethylsiloxane), Analytical Chemistry, Vol. 70, No. 23, 4974–4984 (Dec. 1, 1998) may also be used to produce frame structures including connectors.

Referring again to FIG. 8, according to the present invention a hybridization assay can be performed by providing the generally planar substrate 50 that includes a specimen area 52 and at least one biomolecule 54 on the surface of the planar substrate. As shown in FIG. 9, the frame 56 having at least one fluid connection 62, and preferably a second fluid connection 64 is positioned over the substrate and attached to the substrate so that the frame 56 surrounds at least a portion of the specimen area 52 and the frame and the substrate define a well 60 for holding a fluid.

Figure 10:
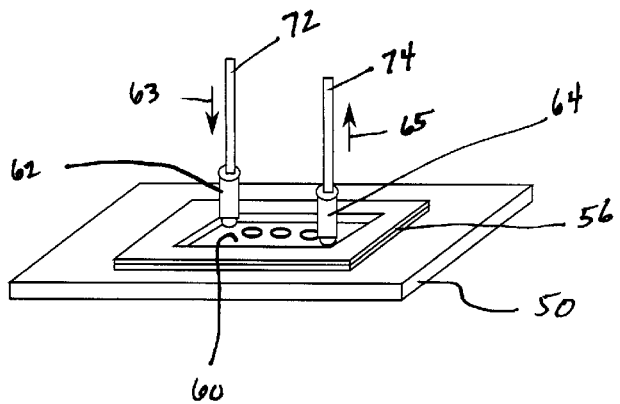
FIG. 10 is a perspective view showing fluid flow through the connectors and tubing attached to the connectors according to another aspect of the invention.

Referring now to FIG. 10, tubing 72 and 74 is connected respectively to connectors 62 and 64. Tubing 72 and connector 74 may be in fluid communication with a supply of wash fluid and/or hybridization fluid (not shown) to supply fluid to the well 60 as indicated by the arrow 63. Tubing 74 and connector 64 may be attached to waste receptacle, vacuum pump or other similar equipment (not shown) to remove waste from the well as indicated by the arrow 65.

In a typical hybridization experiment the specimen area 60 would first be contacted with a wash solution and dried prior to contact with any hybridization solution. Wash solution can be supplied through the supply tubing 72, and the solution can be removed via the waste tubing 74. After washing, the specimen area is typically dried. According to the present invention, drying gases can be supplied through supply tubing 72 to dry the specimen area prior to supplying hybridization solution to the specimen area 52.

After the specimen area 52 has been dried, hybridization fluid can be supplied through the supply line 72, and the hybridization chamber is left undisturbed under conditions and time sufficient to permit hybridization. The hybridization solution can then be removed via the waste tubing 74 with the aid of a pump or vacuum if desired. Thereafter, additional wash steps may be performed.

Figure 11:
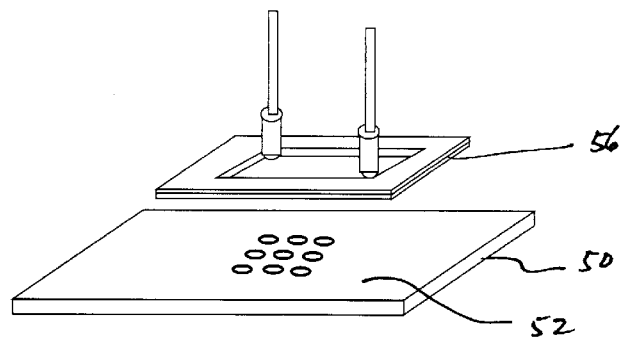
FIG. 11 is a perspective view showing the frame including connectors after removal from the substrate.

After hybridization, washing and drying, as shown in FIG. 11, the frame 56 is removed from the substrate 50, and the frame can be cleaned and reused for another biological experiment. The substrate is then scanned for hybridization analysis.

Another aspect of the invention relates to a kit for performing hybridization assays on biomolecules. According to one aspect, the kit includes a slide for printing a high density array of biomolecules. The kit may also include a preprinted microarray of nucleic acid.

The invention is also useful for performing cell-based assays for detecting and monitoring metabolic changes induced by chemical or biochemical stimuli in biomolecules. It is also within the scope of the invention to utilize a high density chip array for high throughput screening of biomolecules using an imaging system.

It will be apparent to those skilled in the art that various modifications and variations can be made to the present invention without departing from the spirit or scope of the invention. For example, the kits, devices and methods of the present invention may be utilized for a wide variety of experiments utilizing biological fluid. Thus, it is intended that the present invention cover modifications and variations of this invention provided they come within the scope of the appended claims and their equivalents.

What is claimed is:

1. A device for performing biological experiments using fluids comprising:
   a generally planar substrate including a specimen area containing at least one biomolecule; and
   a frame surrounding at least a portion of the specimen area, the frame defining walls of a well for containing a fluid when the frame is in contact with the substrate, the frame including a connector adapted to connect to tubing for supplying fluids to the well, wherein the connector is integrally formed with said frame and selected from the group consisting of male luer fittings, female luer fittings, flanged fittings, flangless fittings, threaded fittings and barbed fittings, and said frame is self-adhering to said substrate.

2. The device of claim 1, wherein the frame includes at least two connectors adapted to connect to tubing for supplying fluids to the well.

3. The device of claim 2, wherein one of the at least two fittings is connected to supply tubing for supplying reagents to the well and one of the at least two fittings is connected to waste tubing for removing fluids from the well.

4. The device of claim 1, wherein the frame is manufactured from an elastomeric material that forms a fluid tight seal with the generally planar substrate.

5. The device of claim 4, wherein the elastomeric material is selected from the group consisting of silicone rubber, poly(dimethylsiloxane), and combinations thereof.

6. The device of claim 1, wherein the frame is sized such that the depth of the well is less than 100 microns.

7. A kit for performing a binding assay comprising:
   a device according to claim 1.

8. The kit according to claim 7, wherein the kit further includes a slide for printing an array of biomolecules.

9. The kit according to claim 7, wherein the kit further includes a DNA microarray.

10. A method of performing biological experiments using fluids comprising:
    providing a generally planar substrate including a specimen area containing at least one biomolecule and a frame including a connector adapted to connect to tubing for supplying fluids to the well, wherein the connector is integrally formed with said frame and selected from the group consisting of male luer fittings, female luer fittings, flanged fittings, flangless fittings, threaded fittings and barbed fittings; and
    placing the frame in contact with the substrate so that the frame surrounds at least a portion of the specimen area and the frame self-adheres to the substrate and defines a well for containing a fluid.

11. The method of claim 10, further comprising the steps of providing a frame including at least two connectors adapted to be connected to tubing;
    connecting supply tubing to one of the connectors to supply fluids to the well; and
    connecting waste tubing to one of the connectors to remove fluids from the well.

12. The method of claim 11, further comprising the steps of:
    supplying wash fluid to the well through the supply tubing and removing the wash fluid from the well through the waste tubing; and
    supplying hybridization fluid to the well through the supply line; and
    removing the hybridization material from the well through the waste line.

13. The method of claim 12, wherein the substrate contains a microarray of biomolecules and the method further includes the step of scanning the microarray for hybridization analysis.

* * * * *